(12) United States Patent
Henson

(10) Patent No.: US 8,343,167 B2
(45) Date of Patent: Jan. 1, 2013

(54) THROMBECTOMY SYSTEM AND METHOD

(75) Inventor: Michael R. Henson, Coto de Caza, CA (US)

(73) Assignee: Reverse Medical Corporation, Irvine, CA (US)

( * ) Notice: Subject to any disclaimer, the term of this patent is extended or adjusted under 35 U.S.C. 154(b) by 406 days.

(21) Appl. No.: 12/187,227

(22) Filed: Aug. 6, 2008

(65) Prior Publication Data
US 2009/0054918 A1 Feb. 26, 2009

Related U.S. Application Data

(60) Provisional application No. 60/963,637, filed on Aug. 6, 2007.

(51) Int. Cl.
*A61B 17/22* (2006.01)
(52) U.S. Cl. ........................................ 606/108; 606/159
(58) Field of Classification Search .................. 606/159, 606/1, 108, 110, 113–114, 127, 200, 216; 148/402; 604/22, 508, 93.01
See application file for complete search history.

(56) References Cited

U.S. PATENT DOCUMENTS

| | | | |
|---|---|---|---|
| 4,706,671 A | 11/1987 | Weinrib | |
| 5,011,488 A | 4/1991 | Ginsburg | |
| 5,102,415 A | 4/1992 | Guenther et al. | |
| 5,895,398 A | 4/1999 | Wensel et al. | |
| 6,530,935 B2 | 3/2003 | Wensel et al. | |
| 6,638,293 B1 | 10/2003 | Makower et al. | |
| 6,740,096 B2 | 5/2004 | Teague et al. | |
| 7,014,623 B2 * | 3/2006 | Prestidge et al. | 604/110 |
| 7,306,683 B2 * | 12/2007 | Cheung et al. | 148/563 |
| 7,744,604 B2 * | 6/2010 | Maitland et al. | 606/108 |
| 2001/0039412 A1 | 11/2001 | Fariabi | |
| 2003/0236533 A1 | 12/2003 | Wilson et al. | |
| 2004/0010280 A1 * | 1/2004 | Adams et al. | 606/194 |

(Continued)

OTHER PUBLICATIONS

International Search Report and Written Opinion corresponding to PCT/US2008/072382 filed Aug. 6, 2008, International Searching Authority dated Nov. 7, 2008.

*Primary Examiner* — Ryan Severson
*Assistant Examiner* — Rachel S Papeika
(74) *Attorney, Agent, or Firm* — K. David Crockett, Esq.; Crockett & Crockett, PC

(57) ABSTRACT

Disclosed is a clot and foreign body removal system, including a catheter with at least one lumen. Located within the catheter is a clot capture wire that is connected to a hub at the proximal end. In one embodiment, the clot capture wire includes a coil made out of an elastic or superelastic material, preferably nitinol. The elasticity or superelasticity of the coil allows it to be deformed within the catheter and to then reform its original coil configuration when the coil is moved outside of the catheter lumen. In another embodiment the coil is a biphasic, shape memory coil, which changes shape upon heating, energy application, or passing an electric current. Once the coil configuration has been established, the coil can be used to ensnare and corkscrew a clot or blockage in a vessel. A clot is extracted from the vessel by moving the clot capture coil and catheter proximally until the clot can be removed completely or released into a different vessel that does not perfuse a critical organ. Foreign bodies are similarly captured by deploying the coil distal to the foreign body and moving the clot capture coil proximally until the foreign body is trapped within the coil. By removing the device from the body, the foreign material is also removed.

6 Claims, 12 Drawing Sheets

U.S. PATENT DOCUMENTS

| | | |
|---|---|---|
| 2004/0133231 A1* | 7/2004 | Maitland et al. .............. 606/200 |
| 2004/0199202 A1 | 10/2004 | Dubrul et al. |
| 2006/0009785 A1 | 1/2006 | Maitland et al. |
| 2006/0253145 A1* | 11/2006 | Lucas .......................... 606/159 |
| 2006/0264821 A1* | 11/2006 | Vo et al. ..................... 604/95.05 |

* cited by examiner

THROMBECTOMY SYSTEM AND METHOD

RELATED APPLICATION

This application claims priority to U.S. Provisional Patent Application No. 60/963,637, filed Aug. 6, 2007, the entire disclosure of which is expressly incorporated herein by reference.

BACKGROUND OF THE INVENTION

1. Field of the Invention

The invention relates to medical devices for percutaneously accessing and performing therapy on body lumens and cavities and, more particularly, to methods and devices for clot or debris removal within the cardiovascular system, peripheral vasculature, or neurovasculature.

2. Description of the Related Art

Thromboembolic disorders, such as occlusive stroke, pulmonary embolism, myocardial infarct, peripheral thrombosis, cerebrovascular occlusion, atherosclerosis, and the like, affect many people. These disorders are a major cause of morbidity and mortality in the United States.

Thromboembolic events are characterized by an occlusion of a blood vessel. The occlusion can be caused by a clot or thrombus, which can be viscoelastic (jelly-like) and is comprised of platelets, fibrinogen, and other clotting proteins. The occlusion can also be more rigid material such as plaque, which has broken off from a vessel wall upstream of the site of the occlusion.

When a clot occludes an artery, tissue ischemia (lack of oxygen and nutrient delivery to the tissue) can develop. The ischemia can progress to tissue infarction (cell death) if the occlusion persists. Infarction does not develop or is greatly limited if the flow of blood is reestablished rapidly. Failure to re-establish blood flow can lead to the loss of limb, angina pectoris, myocardial infarction, stroke, compromised cognitive or neural function, or even death.

Occlusion of the venous circulation by thrombi leads to blood stasis, which can cause numerous problems. The majority of pulmonary embolisms are caused by emboli that originate in the peripheral venous system although occlusions of the cerebrovasculature occur in millions of Americans yearly, often with catastrophic results. Reestablishing blood flow and removal of the thrombus or occlusion is critically important for the well being of these patients.

There are many existing techniques employed to reestablish blood flow in an occluded vessel. One common surgical technique, an embolectomy, involves incising a blood vessel and introducing a balloon-tipped device, such as the Fogarty® catheter, to the location of the occlusion. The balloon is then inflated at a point beyond the clot and used to translate the obstructing material back to the point of incision. The surgeon can, then, remove the obstructive material. While such surgical techniques have been useful, exposing a patient to surgery may be traumatic and best avoided when possible. Additionally, the use of a Fogarty catheter is problematic because of the great risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel, typically through an introducing catheter. The balloon-tipped catheter is then advanced to the point of the occlusion and inflated in order to dilate the stenosis. Balloon angioplasty is appropriate for treating vessel stenosis but is not effective for treating acute thromboemboli.

Another technique is thrombolysis wherein a thrombolytic agent (e.g., streptokinase, urokinase, tissue plasminogen activator (TPA) is administered systemically or locally through a catheter. Unfortunately, thrombolysis typically takes hours to days to be successful. Additionally, thrombolytic agents can sometimes cause hemorrhage and in many be contraindicated in certain patients.

U.S. Pat. Nos. 4,706,671 (Weinrib) and 5,011,488 (Ginsburg) both describe the use of percutaneously inserted catheter-based devices for removal of thromboembolic material. In particular, U.S. Pat. No. 4,706,671 teaches the use of a hollow flexible elastomeric material to form the shape of the coiled section. The coiled section is hollow to allow for the insertion of a liquid into the hollow center such that the coils become stiff. U.S. Pat. No. 5,011,488 teaches the use of a coiled section that is fixed on both the proximal and distal ends such that the operator of the device can change the shape and size of the coils. In addition, U.S. Pat. Nos. 5,895,398 (Wensel et al.) and 6,530,935 (Wensel et al.) describe a clot and foreign body removal device which comprises a catheter having at least one lumen and a clot capture coil that is connected to an insertion mandrel. In one embodiment, the clot capture coil is made out of a solid elastic or superelastic material which has shape memory, preferably nitinol. The elasticity or superelasticity of the coil allows it to be deformed within the catheter and to then reform its original coil configuration when the coil is moved outside of the catheter lumen. In another embodiment the coil is a biphasic coil which changes shape upon heating or passing an electric current. In operation, the catheter is advanced through the clot and the mandrel with the clot capture coil attached is advanced through the catheter and out of its distal end. The superelastic or biphasic coil then assumes its coiled configuration. Once the coil configuration has been established, the coil can be used to ensnare and corkscrew a clot in a vessel. A clot is extracted from the vessel by moving the clot capture coil and catheter proximally until the clot can be removed or released into a different vessel that does not perfuse a critical organ. Foreign bodies are similarly captured by deploying the coil distal to the foreign body and moving the clot capture coil proximally until the foreign body is trapped within the coil. By removing the device from the body, the foreign material is also removed.

Foreign bodies introduced into the circulation can be fragments of catheters, pacemaker electrodes, guide wires, and erroneously placed embolic material such as thrombogenic coils. The available retrieval devices for the removal of foreign bodies include devices which form a loop that can ensnare the foreign material by decreasing the size of the diameter of the loop around the foreign body. The use of such removal devices can be difficult in at least some cases and sometimes unsuccessful.

Thus, there exists a need for the development of a device that can be easily deployed into the circulatory system for the removal of various materials including viscoelastic clots and foreign bodies. There is also a need for a device that can be used as a temporary arterial or venous filter to capture and remove thromboemboli formed during endovascular procedures.

U.S. Pat. No. 5,102,415 (Guenther et al.) describes a system for removing obstructions from blood vessels comprising balloon catheter and another catheter having an expandable tip, which receives the obstruction. The balloon catheter is passed through the obstruction while the balloon is deflated. The balloon is then inflated and the tip of the catheter is expanded. The balloon is then moved proximally so that the obstruction is pulled into the expanded tip of the catheter. A problem with the system of U.S. Pat. No. 5,102,415 is that the interaction between the balloon catheter and the leading edge of the catheter may tend to shear off portions of the obstruction. This can cause obvious problems when working in sensitive vascular areas since pieces of the obstruction can migrate and cause further obstruction with adverse ischemic consequences.

A need, therefore, remains for improved obstructive matter removal technology, which allows a device to be percutaneously or surgically introduced, transluminally advanced to a target body lumen and across or through the obstructive matter (e.g., a thrombus), thereafter expanded and then retracted and removed along with the obstructive matter.

SUMMARY OF THE INVENTIONS

The present invention provides systems and methods for removing obstructive matter, such as thrombus, foreign objects, etc., from blood vessels or other natural or man-made body lumens (e.g., ureter, urethra, bile duct, pancreatic duct, hepatic duct, surgically created bypass tracts, etc.).

In accordance with the present invention, there is provided a system for removing thrombus or other obstructive material from a natural or man-made body lumen in a human or non-human animal subject, such system comprising (A) a flexible catheter having a lumen and a distal opening in communication with said lumen; (B) an elongate member having a distal end, said elongate member being advanceable through the lumen of the catheter and out of the distal opening; (C) an obstructive material engaging structure located at or near the distal end of the elongate member, said obstructive material engaging structure being transitionable in response to energy delivered to the obstruction engaging structure from a collapsed configuration wherein the obstruction engaging structure is substantially linear and advanceable through the obstructive material to an expanded configuration wherein the obstructive material engaging structure will engage the obstructive material; and (D) a source of energy (e.g., electrical current, heat, light, ultraviolet light, etc) connected (e.g., by way of a wire, light guide or other energy delivering connection) to the obstructive material engaging member, such source of energy being operative to deliver to the obstructive material engaging structure energy which will cause the obstructive material engaging structure to transition from its collapsed configuration to its expanded configuration. In some embodiments of this system, the obstructive material engaging structure may comprises a shape memory material (e.g., a shape memory alloy such as nickel-titanium or shape memory polymer) that will expand from the collapsed configuration to the expanded configuration in response to the delivery of energy which causes a temperature change or other shape-changing modification in the shape memory material. Also, in some embodiments, the elongate member may be substantially formed of shape memory material (e.g., a wire, strand, elongate extrusion or cable formed of a shape memory alloy such as nickel-titanium or shape memory polymer) and the energy may be applied selectively to a particular segment of the elongate member to cause that segment to deform or change shape (e.g., could or twist) to create the obstructive material engaging member.

Further in accordance with the invention, there is provided a method for removing obstructive material from a natural or man-made body lumen in a human or non-human animal subject using an obstructive material removal system that comprises (i) a flexible catheter having a lumen and a distal opening in communication with said lumen, (ii) an elongate member having a distal end, said elongate member being advanceable through the lumen of the catheter and out of the distal end opening, (iii) an obstructive material engaging structure located at or near the distal end of the elongate member, said obstructive material engaging structure being transitionable in response to energy delivered to the obstruction engaging structure from a collapsed configuration wherein the obstruction engaging structure is substantially linear and advanceable through the obstructive material to an expanded configuration wherein the obstructive material engaging structure will engage the obstructive material and (iv) a source of energy connected to the obstructive material engaging member. In this method, the catheter is advanced to a position within the body lumen without causing the catheter to pass through the obstructive material. Thereafter, the elongate member, with the obstructive material engaging member in its collapsed configuration, is advanced through the catheter lumen and out of the distal opening of the catheter and through the obstructive material to a position where the distal end opening of the catheter is on one side of the obstructive material and the obstructive material engaging member is on the other side of the obstructive material. Then, energy is delivered from the energy source to the obstructive material engaging member causing the obstructive material engaging member to transition to its expanded configuration. Thereafter, the obstructive material engaging member is moved, while in its expanded configuration, toward the obstructive material until it engages the obstructive material. The system, along with the obstructive material engaged by the obstructive material engaging member, are then removed from the body lumen.

Further aspects, details and embodiments of the present invention will be understood by those of skill in the art upon reading the following detailed description of the invention and the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION AND EXAMPLES

Figure 1:
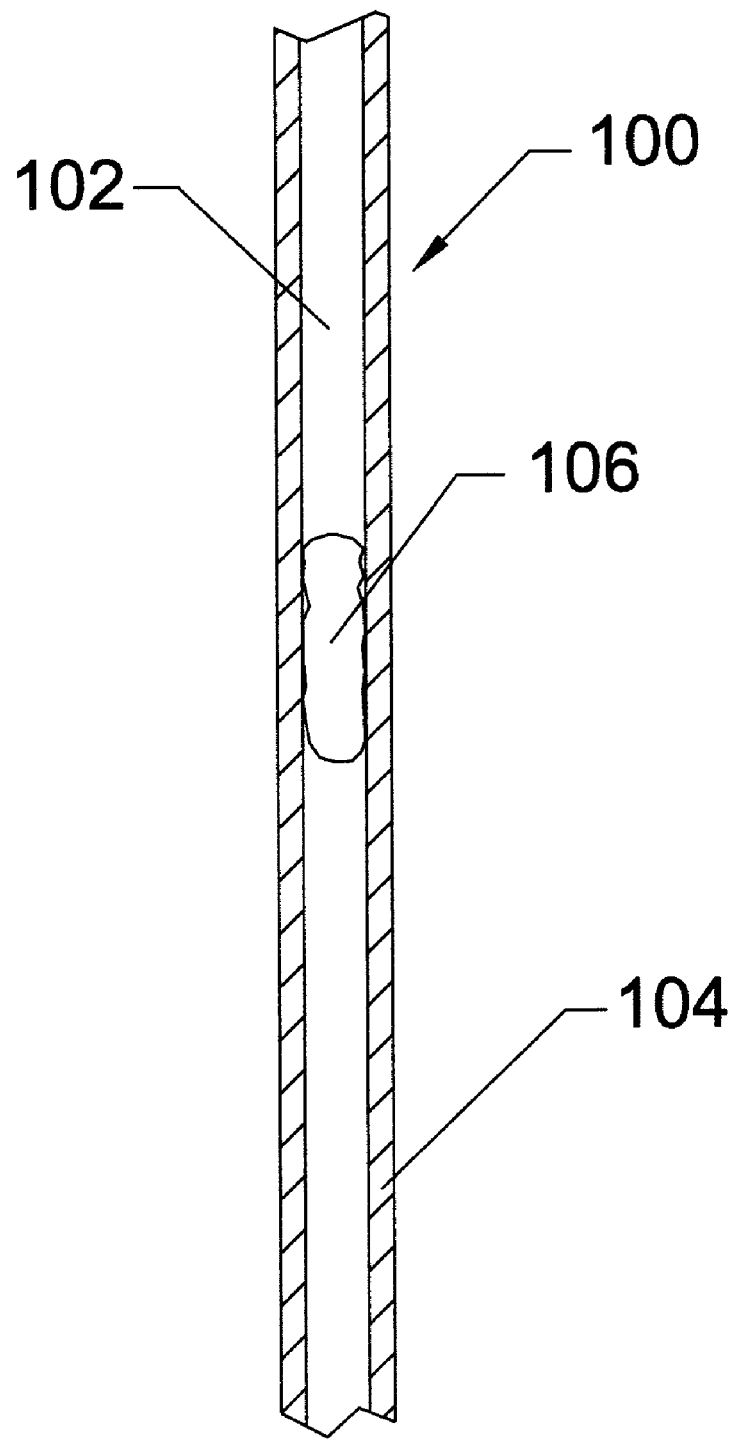
FIG. 1 is a schematic representation of a blood vessel in a mammalian body, wherein the blood vessel is being occluded, at least partially, by thrombus, clot, plaque, or other obstruction.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

The present invention is directed to methods and devices for removing obstructions from blood vessels. The device may be used to retrieve and remove clots and other biological obstructions. The device may also be used to retrieve embolic coils and the like which have been misplaced or have migrated to an undesirable location.

In an embodiment of the invention, a catheter is advanced to the region of an obstruction. The obstruction can reside within a body vessel or lumen. The body vessel or lumen can be that of a human, mammal, or other animal. The body vessel can be a blood vessel, a lymphatic duct, a bile duct, a ureter, or any other body vessel. A blood vessel can be either a vein or an artery. The obstruction can be partial or total. The obstruction can have a central orifice or a through orifice that is disposed closer to one side of the vessel than another side (off-center). The catheter can be advanced translumininally, transvascularly, endovascularly, or the like from the access site to the target site. The catheter can be advanced under fluoroscopic guidance with the aid or radiopaque markers affixed to the catheter. At least some of the radiopaque (RO) markers can be affixed at or near the distal end of the catheter.

In an embodiment, the catheter or thrombectomy device can comprise a guiding catheter, or microcatheter, and a central wire. The central wire can comprise shape memory alloys such as nitinol. The central wire can comprise radiopaque markers fabricated from materials such as, but not limited to, tantalum, platinum, iridium, gold, and the like. The central wire can also comprise Ohmic, or resistive, heating elements such as nickel-chromium wire exhibiting high resistance and advantageous heat generation given an electrical current applied across the Ohmic-heating element. The central wire can comprise thermal insulation. The central wire can comprise one or more electrical conductors, leads, bus lines, or the like. The central wire can be configured to pierce or advance through a clot or other obstruction with a conical, sharpened, or small diameter distal tip. The central wire can comprise one or more radiopaque markers. The central wire can be configured to be straight with a certain amount of flexibility and column strength during advancement to a target site and across an obstruction. Upon heating of the central wire to a temperature above a certain transition temperature, the distal end of the central wire can form a coil, a complex coil, a conical coil, a rat's nest, a ball, or other structure. The diameter of the structure formed above transition temperature can be greater than, equal to, or less than the diameter of the parent vessel or lumen. Heating and restructuring of the distal end of the central wire can be accomplished by application of electrical, thermal, electromagnetic, sound, or other energy to the distal end of the catheter. In certain embodiments, the energy can be applied to the proximal end of the catheter and then be transmitted over appropriate energy conduits, for example electrical leads or an electrical bus, to the distal end of the catheter.

The coil structure at the distal end of the wire advantageously comprises sufficient internal strength that, when it is pulled through a thrombus structure, it can retain its shape and deform, excise, cut, core, or otherwise remove the thrombus structure from the vessel, in whole or in part.

The coaxial catheter, microcatheter, guide catheter, or receiving catheter, herein identified as the receiving catheter, can comprise a distal end that is radially expandable. The receiving catheter distal end can comprise rails, ribs, stays, battens, reinforcements, or bands of metal that are biased outwardly and are selectively restrained inwardly with an outer, coaxial, retractable sheath. In another embodiment, the receiving catheter distal end can comprise ribs or bands of metal that can be biased outwardly using shape memory properties upon energy delivery from the proximal end of the catheter or directly into the target site. Exemplary materials for use in the receiving catheter distal end include nitinol, stainless steel, titanium, cobalt nickel alloys, or the like. Energy delivery from the proximal end, for the purpose of forming coils in the wire or expanding the receiving catheter distal end, includes electrical energy, either AC or DC in voltages ranging from 1.2 Volts to 240 Volts. Energy delivery, for both coil configuration and catheter expansion, at the distal end includes microwave, high intensity focused ultrasound (HIFU), radiofrequency (RF), or other types of energy. In another embodiment, the receiving catheter distal end can be fabricated with a malleable reinforcement embedded within a polymeric surround, wherein the malleable reinforcement is sufficiently strong so as to substantially control the configuration of the polymeric surround. In an exemplary embodiment, the polymeric surround is fabricated from polyethylene with a total thickness of 0.008 to 0.020 inches and an annealed stainless steel coil with thickness of 0.002 to 0.005 inches and a width of 0.020 to 0.125 inches is embedded therein. The spacing between the coil turns can range from 0.010 to 0.250 inches. The malleable thin wall distal end can be folded along longitudinal creases to reduce its diameter. A high-pressure angioplasty-type balloon disposed inside the lumen of the distal end can be inflated to radially expand the catheter. The angioplasty-type balloon, referred to as a dilation balloon, can be disposed on the central wire or a separate catheter placed alongside the wire.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

The invention, which is generally termed a catheter, sheath, or wire, can be described as being an axially elongate hollow tubular structure having a proximal end and a distal end. The axially elongate structure further has a longitudinal axis and has an internal through lumen that extends from the proximal end to the distal end for the passage of instruments, fluids, tissue, or other materials. The axially elongate hollow tubular structure is generally flexible and capable of bending, to a greater or lesser degree, through one or more arcs in one or more directions perpendicular to the main longitudinal axis. As is commonly used in the art of medical devices, the proximal end of the device is that end that is closest to the user, typically a cardiologist, surgeon, radiologist, interventional neuroradiologist, or electrophysiologist. The distal end of the device is that end closest to the patient or that is first inserted into the patient. A direction being described as being proximal to a certain landmark will be closer to the user, along the longitudinal axis, and further from the patient than the specified landmark. The diameter of a catheter is often measured in "French Size" which can be defined as 3 times the diameter in millimeters (mm). For example, a 15 French catheter is 5 mm in diameter. The French size is designed to approximate the circumference of the catheter in mm and is often useful for catheters that have non-circular cross-sectional configurations. While the original measurement of "French" used π (3.14159 . . . ) as the conversion factor between diameters in millimeters (mm) and French, the system has evolved today to where the conversion factor is 3.0.

FIG. 1 is a schematic representation of a blood vessel 100 in a mammalian body, wherein the blood vessel 100 is being occluded, at least partially, by thrombus, clot, plaque, or other obstruction 106. The blood vessel 100 further comprises a vessel lumen 102 and a wall 104. The blood vessel 100 can be a vein or an artery. The blood vessel can be as large in diameter as the aorta, which can range from 1.5 cm to 3.5 cm diameter. The vessel can be as small in diameter as a coronary artery (2 to 4 mm diameter) or a vessel in the neurovasculature (1 to 4 mm diameter). The vessel lumen 102 generally comprises blood (not shown), which should be flowing therethrough. The presence of the obstruction 106 can compromise blood flow and result in tissues downstream not receiving adequate oxygenation or nutrition for continued health. The compromised blood flow can lead to tissue ischemia and ultimately cell death if the compromised blood flow remains untreated for an extended period of time.

Figure 2:
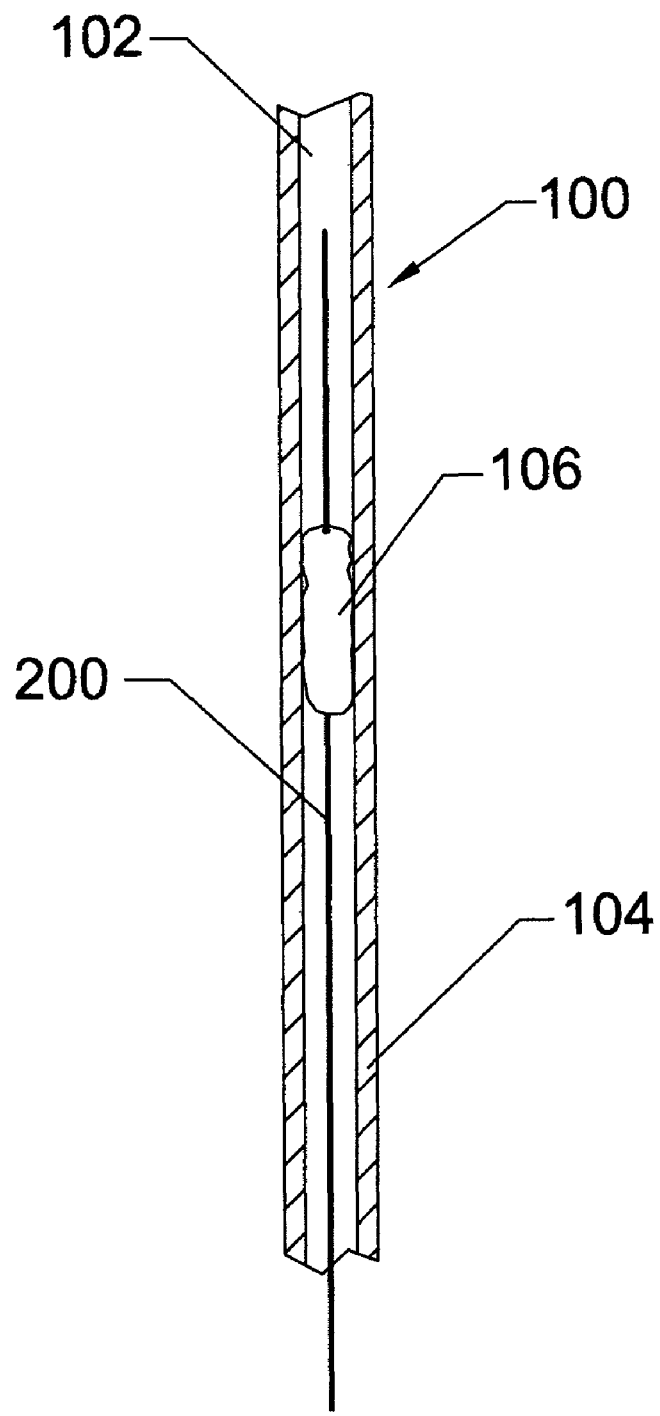
FIG. 2 is a schematic representation of a blood vessel in a mammalian body, wherein a blood vessel occlusion has been traversed by the distal end of a clot removal apparatus, according to an embodiment of the invention.

FIG. 2 is a schematic representation of a blood vessel 100 in a mammalian body, wherein a blood vessel occlusion 106 has been traversed by a distal end of a substantially straight clot removal apparatus 200. The blood vessel occlusion 106 resides within the vessel lumen 102 of the blood vessel 100 and extends all the way to the walls 104 of the blood vessel. The clot removal apparatus wire 200 is generally straight and its longitudinal axis generally follows the longitudinal axis of the blood vessel 100.

The clot removal apparatus 200 is configured straight during the insertion phase. The clot removal apparatus 200 is advantageously flexible but retains significant column strength so it can be advanced through thrombus material. The clot removal apparatus 200 can be a single structure fabricated from shape memory nitinol or it can be a composite structure. The clot removal apparatus 200 can comprise an external coil surround (refer to FIG. 11) that covers all or a portion of a central core portion of the clot removal apparatus 200. The clot removal apparatus 200 can have a length ranging from about 10-cm to 250-cm, preferably between around 25 and 175-cm, and more preferably between about 50 and 150-cm. The diameter of the clot removal apparatus 200 in the region where it pierces the obstruction 106 can range between about 0.002 inches and 0.040 inches, and preferably between about 0.005 and 0.030 inches, with a target range of between about 0.007 and 0.013 inches.

The shape memory transition temperature, more specifically the austenite finish temperature ($A_f$), can range between about 25 degrees centigrade to around 32 degrees centigrade if body heat transition is used to configure the coil. The $A_f$ can also range from around 37 degrees centigrade to as high as about 45 degrees centigrade if Ohmic heating is used. In a preferred embodiment for the Ohmic heating system, the austenite finish temperature can range from about 39 to 44 degrees centigrade while the austenite start temperature ($A_S$) can range from about 35 to 42 degrees centigrade. Hysteresis effects can be used to maintain the deformed non-straight coil shape even when heating energy is removed since the martensite start ($M_s$) temperature is generally below the austenite finish ($A_f$) temperature.

The clot removal apparatus 200 can be fabricated from equiatomic or nickel-rich nitinol. The nitinol is a nickel titanium alloy, which contains approximately 50% to 55.6% nickel. In a preferred body heat transition embodiment, the nitinol can be heat treated to set the transition temperature at about 28 to 32 degrees centigrade. Shape setting of the clot removal apparatus 200 into its activated configuration involves heating the clot removal apparatus 200 when constrained about a mandrel or fixture that forces the clot removal apparatus 200 into its substantially non-straight final shape, such as a coil, etc. The heating can be performed at temperatures ranging from about 480 degrees centigrade to 550 degrees centigrade with a preferred temperature range of about 500 to 525 degrees centigrade. The heating time can range from about 3 minutes to about 15 minutes or longer, although increased heating time tends to increase the austenite finish transition temperature (Af). Following the prescribed heating time, the clot removal clot removal apparatus 200 and its mandrel are removed from the heating system and quenched in water or other liquid at about room temperature, for example about 22±20 degrees centigrade. The heating system can be an oven, a convection oven, a sand bath, a salt bath, or the like.

Figure 3:
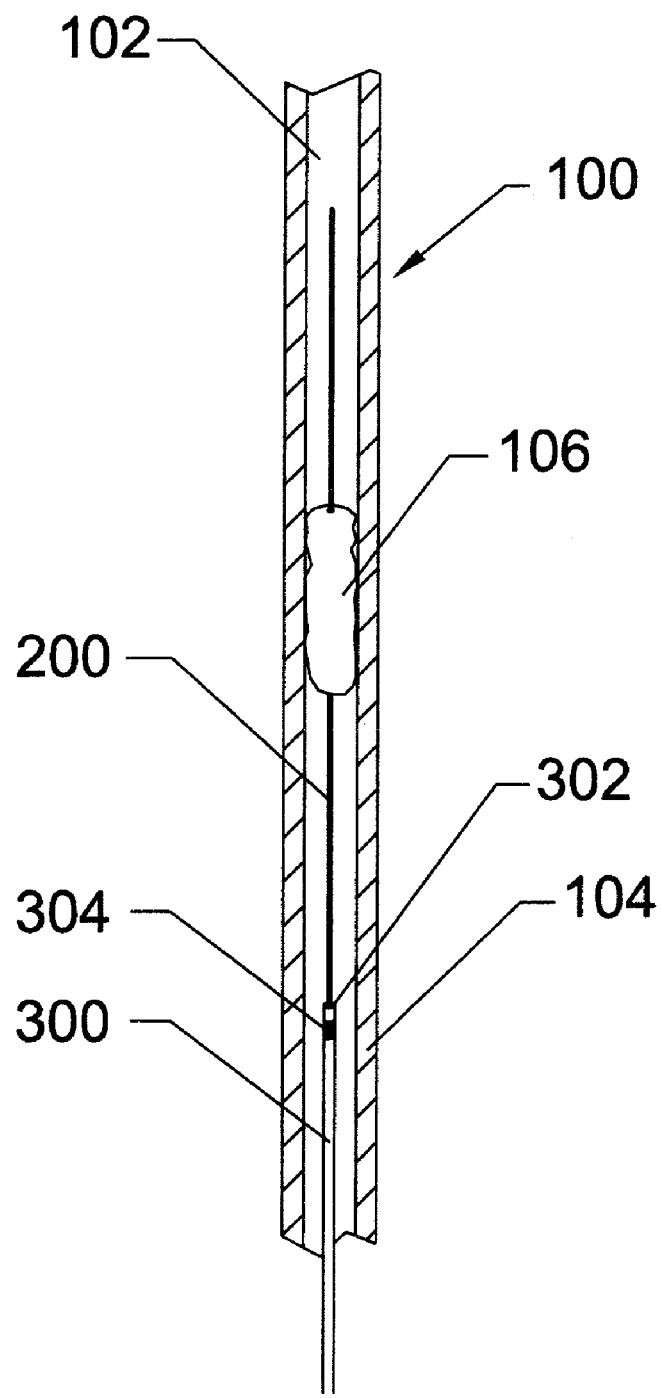
FIG. 3 is a schematic representation of the blood vessel of FIG. 2, wherein the clot removal apparatus further includes a coaxial catheter, which is advanced proximally to the occlusion, according to an embodiment of the invention.

FIG. 3 is a schematic representation of the blood vessel 100 of FIG. 2, wherein the clot removal apparatus 200 further includes a coaxial catheter 300, further comprising a central lumen 302, which is advanced proximally to the occlusion 106. The catheter 300 is slidably disposed over the clot removal apparatus 200 within the central lumen 302 of the catheter 300. The catheter 300 can be a guiding catheter, a microcatheter such as is used in the neurovasculature and having continuously or discreet regions of progressively greater flexibility moving from the proximal to the distal end, or the like. The catheter 300 can be configured to fit within the vessel lumen 102 and may have increasing stiffness moving from proximal to distal to permit guidance and pushability. The catheter 300 can have a length ranging from about 50 cm to about 150 cm. The wall thickness of the catheter 300 can range from about 0.003 to 0.020 inches, and the wall thickness can vary along the length of the catheter 300. The inner lumen 302 of the catheter 300 can have a diameter ranging from about 0.005 to 0.025 inches with a preferred range of about 0.008 to 0.020 inches.

The catheter 300 can further comprise radiopaque markers 304, for example rings or bands of polymer or metal, comprising materials such as, but not limited to, platinum, platinum iridium, tantalum, gold, barium sulfate, or the like, affixed at or near the distal end of the catheter 300 to assist in manipulation and location under fluoroscopy. The radiopaque (RO) markers 304 can have lengths ranging from about 0.010 inches to 0.100 inches with wall thicknesses ranging from about 0.002 to 0.015 inches.

The clot removal apparatus 200 can be extended out the distal end of the catheter 300 or it can be withdrawn partially or completely inside the catheter 300. The catheter 300 can be fabricated from polymeric materials such as, but not limited to, Pebax, polyethylene, polyurethane, PEEK, polypropylene, Hytrel, polyimide, polyamide, or the like. The catheter 300 can further be built up with inner and outer layers of polymer and a central reinforcing layer of coil or braid, fabricated from materials such as, but not limited to, stainless steel, PEN, polyethylene terephthalate (PET), or the like.

The proximal end of the catheter 300 can be terminated with a hub or other structure comprising a Luer fitting, bayonet-mount, hemostasis valve, stopcock, or the like.

Figure 4:
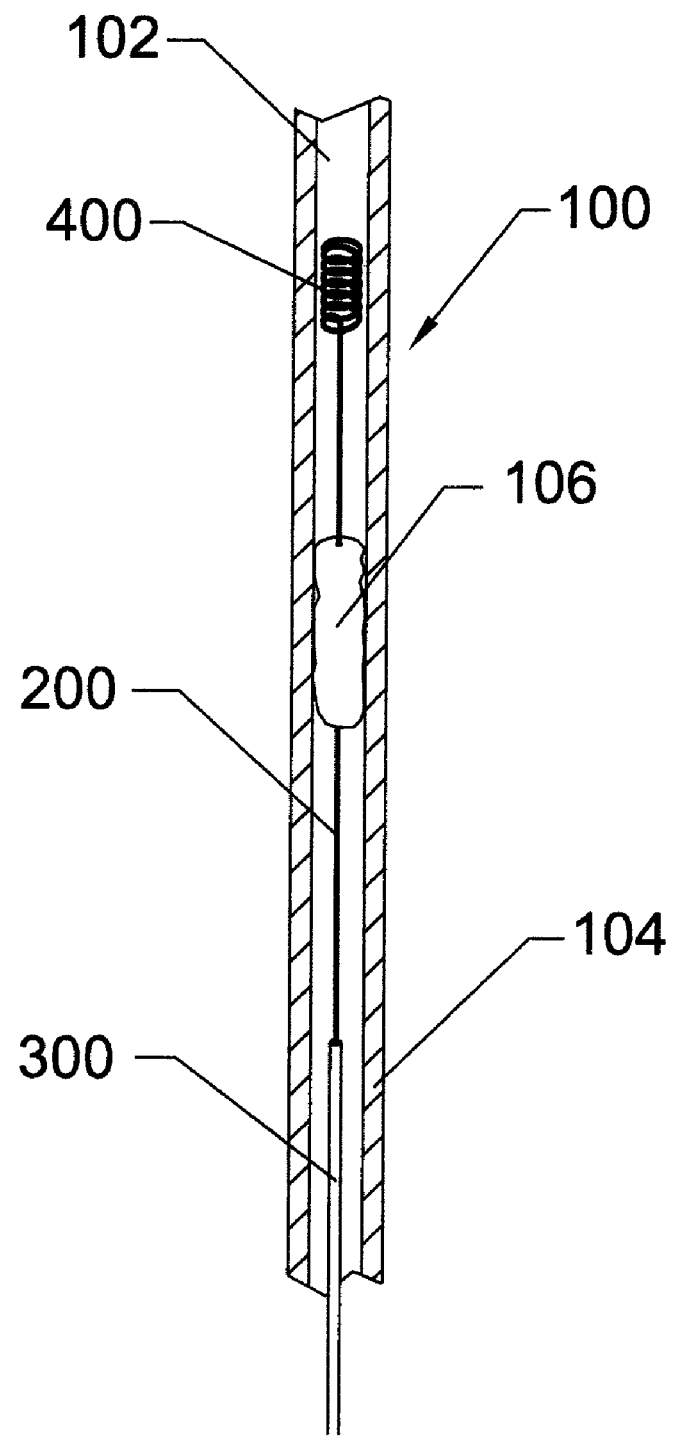
FIG. 4 is a schematic representation of the blood vessel and apparatus in FIG. 3, wherein a distal segment of the clot removal apparatus has been re-configured into a coil, according to an embodiment of the invention.

FIG. 4 is a schematic representation of the blood vessel 100 and clot removal apparatus 200, wherein a distal segment of the clot removal apparatus 200 has been re-configured into a coil 400. The clot removal apparatus 200, having its distal end positioned distal to the obstruction 106, relative to the operator, has now been activated by heating or other means to cause the clot removal apparatus 200 to reconfigure into the coil 400. The coil 400 can have from about 1 to 40 turns and can be cylindrical, conical, ball shaped, irregularly shaped, or possess any shape suitable for effectively expanding its diameter and ability to withdraw the clot 106 proximally. The coil and coil region 400 can be integral, or separately attached, to the clot removal apparatus 200. The coil 400 is formed when the shape memory material, for example nitinol, is heated either by the blood or by energy imparted thereon. Electrical energy can be imparted to the coil 400 through the clot removal apparatus 200 by means of electrical conductors, preferably insulated or isolated electrically. At least one and optionally two or more conductors can be disposed along the length of the clot removal apparatus 200 so that electrical power can be applied at the proximal end of the clot removal apparatus 200 and transmitted along the length of the clot removal apparatus 200 to be delivered to the coil 400 or adjacent heating element. The diameter of the coil 400 should approximate that of the vessel lumen 102 but can also be smaller. Typical coil 400 diameters can range between about 2 mm and 10 mm with a preferred range of about 3 mm to 5 mm in the cerebrovascular setting, for example. The number of turns of the coil 400 can range from about 1 to 15 with a preferred range of about 2 to 8.

Figure 5:
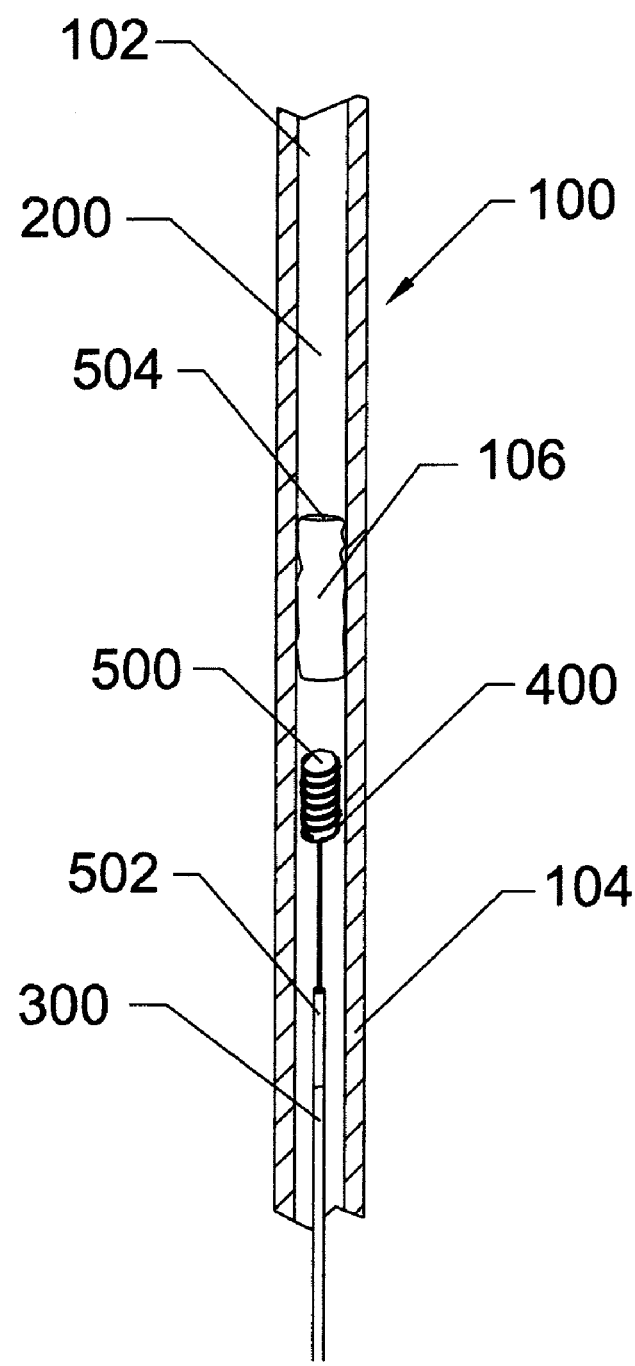
FIG. 5 is a schematic representation of the blood vessel and apparatus in FIG. 4, wherein the coiled distal segment of the clot removal apparatus has been withdrawn proximally through the occlusion so as to core or remove a portion or all of the occlusion, according to an embodiment of the invention.

FIG. 5 is a schematic representation of the blood vessel 100 and clot removal apparatus 200 in FIG. 4, wherein the coiled distal segment 400 of the clot removal apparatus 200 has been withdrawn proximally through the occlusion 106 so as to remove a core portion 500 or all of the occlusion 106. The coil 400 is illustrated residing proximally to the location of the occlusion 106 along with the retrieved piece of occlusion, clot, or thrombus 500. The distal end 502 of the receiving catheter 300 is illustrated in its radially collapsed configuration. The expandable distal region 502 of the receiving catheter 300 can be integral to, or separately affixed to, the distal end of the receiving catheter 300. The occlusion 106, following proximal withdrawal of the coil 400, comprises a central opening, core, or lumen 504, through which blood can now flow without the effect of stenosis. The larger the diameter of the coil 400 relative to the vessel lumen 102, the greater the amount 500 of the thrombus 106 can be removed. In certain method embodiments, it may be beneficial to remove smaller amounts 500 of thrombus 106 followed by secondary treatments to remove successively larger portions 500 of the thrombus 106. Electrocautery methodology, delivering coagulation or cutting current to the coil 400 from the proximal end of the system, can be used to modify the clot removal capabilities of the device.

Figure 6:
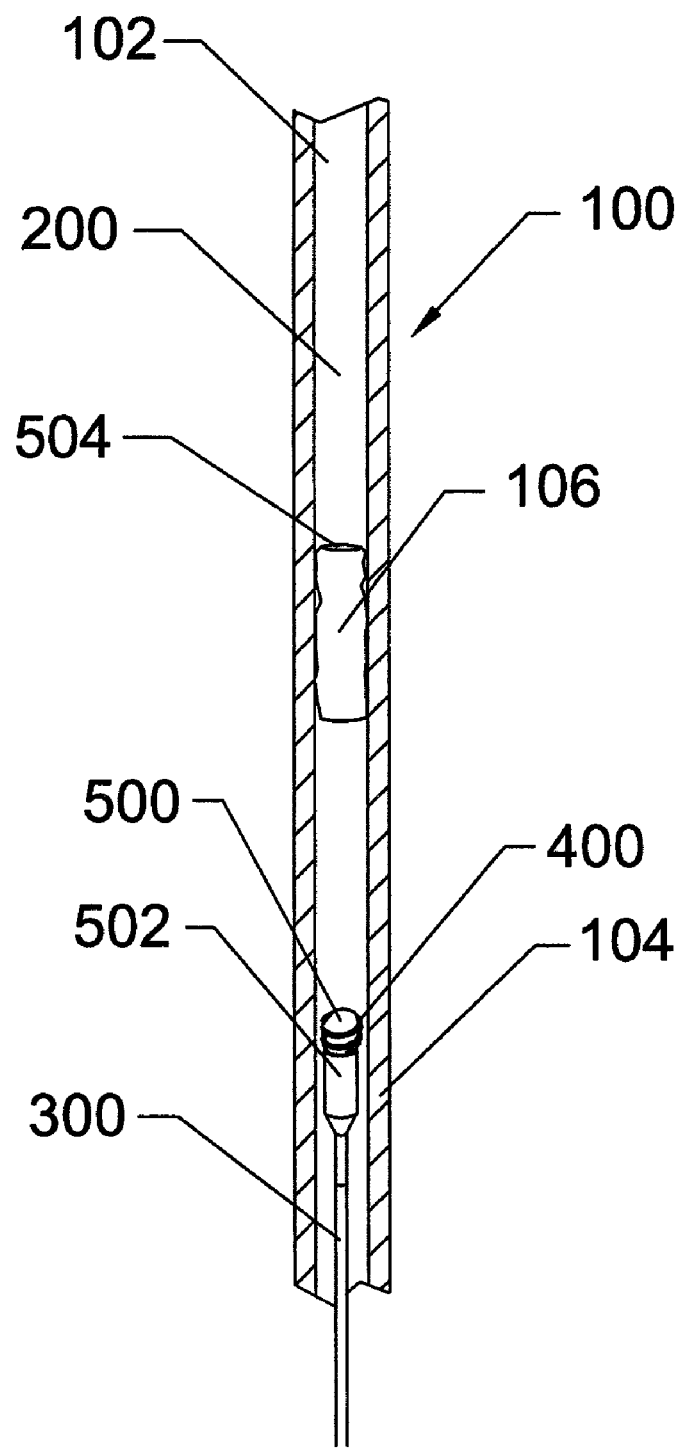
FIG. 6 is a schematic representation of the blood vessel and apparatus in FIG. 5, wherein the distal end of the coaxial catheter has been expanded to envelop all, or a portion, of the occlusion removed by the coiled distal segment, according to an embodiment of the invention.

FIG. 6 is a schematic representation of the blood vessel 100 and clot removal apparatus 200, wherein the distal end 502 of the coaxial catheter 300 has been expanded to envelop all, or a portion, of the occlusion 500 removed by the coiled distal segment 400. The central opening or lumen 504 of the obstruction 160 provides reduced resistance to blood flow through the vessel 100. The clot removal apparatus 200 has been withdrawn proximally so that all but a small portion of the retrieved occlusion 500 and the coil 400 have been enveloped and retrieved within the catheter 300. The expandable region 502 at the distal end of the retrieval catheter 300 can have been expanded due to shape-memory forces acting in response to applied heat or energy, due to withdrawal of an external sheath to allow an elastomeric structure to expand outward, due to passive "shoehorning" of the coil 400 and retrieved clot 500 into the expandable region 502, or due to radially outward dilation forces generated by an internal dilator (not shown), either removable or non-removable. The internal dilator can be a balloon catheter coaxially mounted around, or co-inserted in a parallel fashion alongside, the clot retrieval clot removal apparatus 200. In other embodiments, the dilatation means may rely on axial compression of a braid to expand its diameter, or it may be a translation dilator wherein an inner tube is advanced longitudinally to expand an elastomeric small diameter tube, as described in U.S. Pat. No. 7,309,334, issued on Dec. 18, 2007, the entirety of which is hereby incorporated herein by reference. Dilation may also occur as a result of unfurling a thin-film wrapped tube or by rotation of a series of hoops so that their alignment is at right angles to the long axis of the catheter. The shoehorn effect, described earlier in this paragraph, can be generated because the coil 400 is affixed to the clot removal apparatus 200 at a single point and is able to elongate and constrict inward somewhat under proximal axially directed loading. This constriction can force the excised clot or occlusion 500 to also contract radially to fit within the expandable part 502 of the catheter 300.

Figure 7:
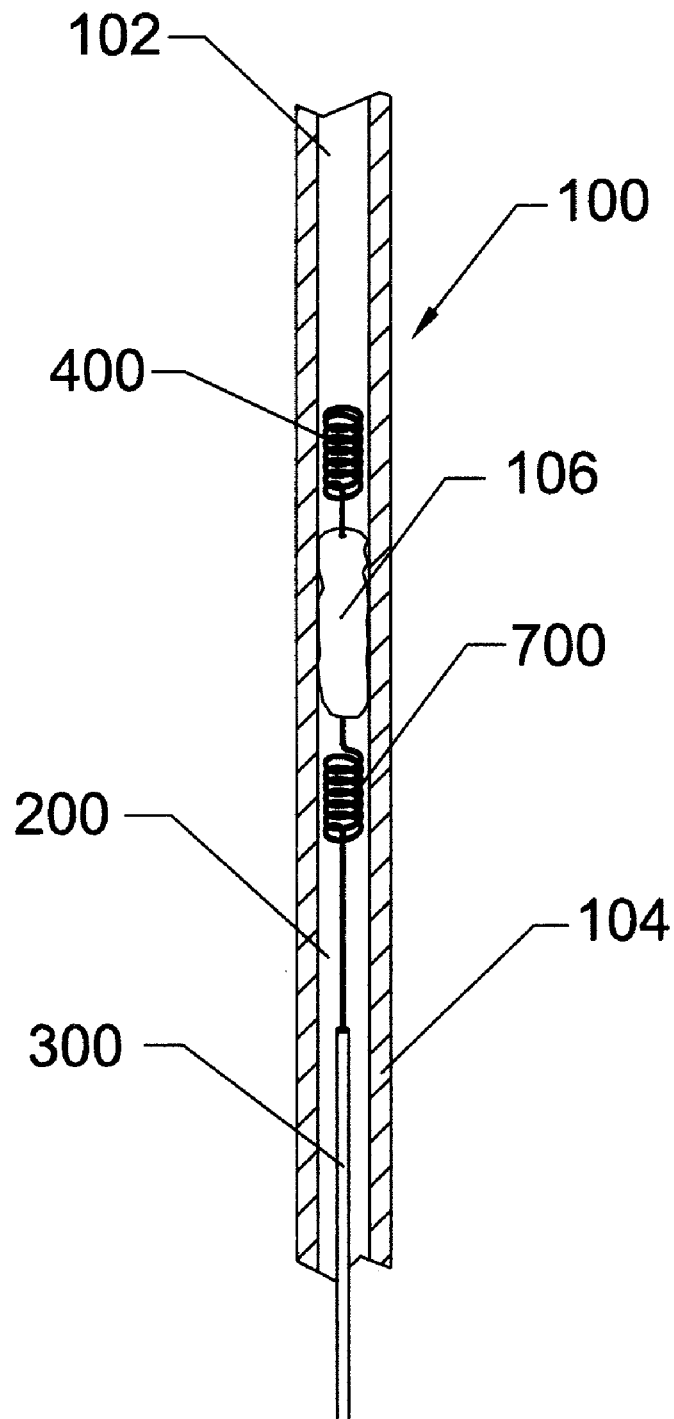
FIG. 7 is a schematic representation of the blood vessel and apparatus in FIG. 6, wherein a region of the clot removal apparatus, disposed proximal to the occlusion, has been reconfigured into a coil so that the occlusion is sandwiched between the proximal and distal coils, according to an embodiment of the invention.

FIG. 7 is a schematic representation of the blood vessel 100 and apparatus 200, wherein a region of the clot removal apparatus 200, disposed proximal to the occlusion 106, has been reconfigured into a coil 700 so that the occlusion 106 is sandwiched between the proximal 700 and distal 400 coils. The proximal coil 700 can be configured to expand separately or at the same time as the distal coil 400. Different coil 400 and 700 expansion times can be generated by separate electrical connections to the proximal end of the clot removal apparatus 200 wherein only one is activated at a time. In other embodiments, the austenite finish temperature of the two coils 400 and 700 can be different to allow one to expand before the other. Using this system with the proximal coil 700 and distal coil 400, it may be possible to eliminate the catheter 300 or to use a larger catheter disposed far proximally to the target occlusion 106 in a correspondingly larger vessel. In another embodiment, the proximal coil 700 can prolapse at its outermost aspect to encompass and surround the excised region of occlusion 500. In yet another embodiment, the distal coil 400 can expand within the occlusion 106 and thereby grab and embed itself within the occlusion 106 to facilitate removal of the mass 500.

Figure 8:
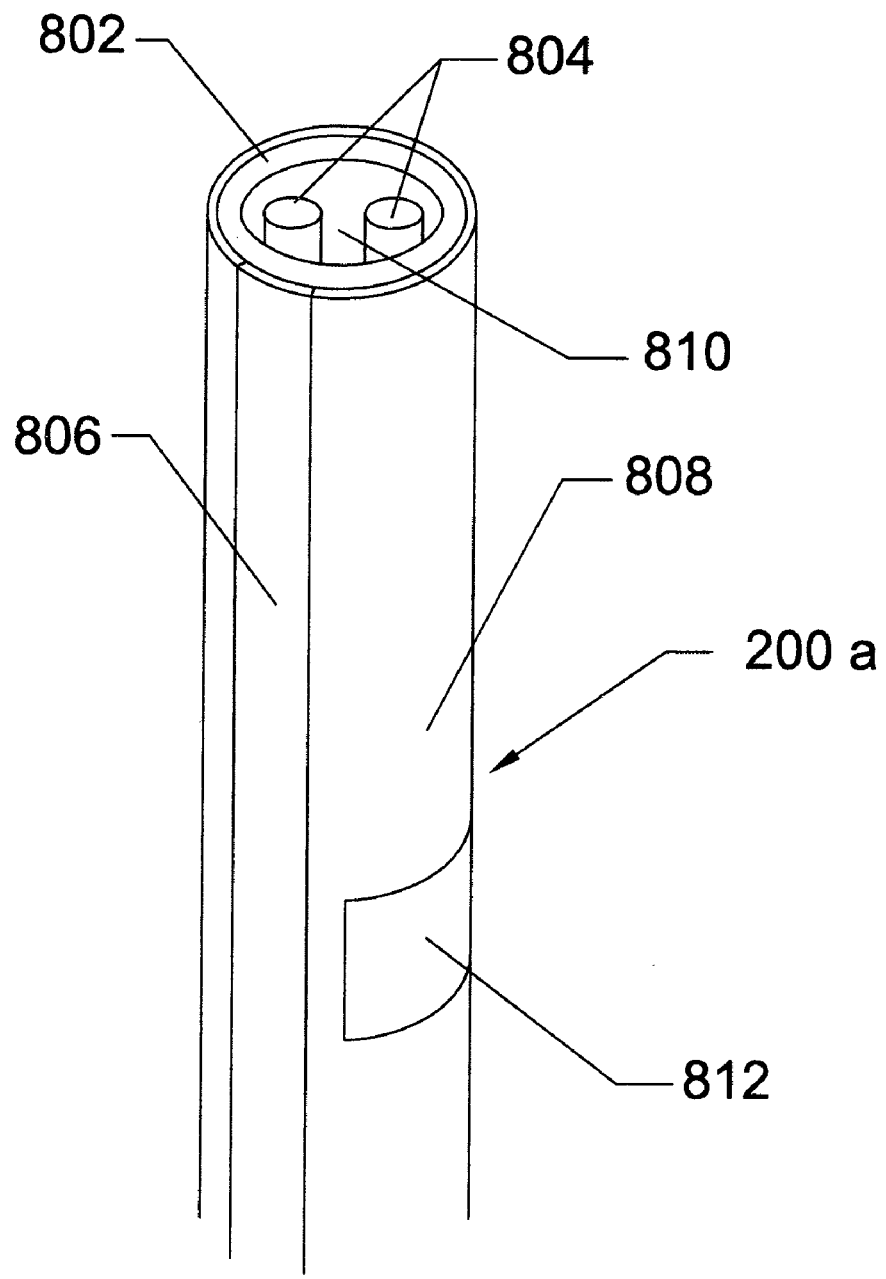
FIG. 8 is an illustration of a cross-section of the clot removal apparatus showing the shape memory element, a heating element, an insulation element, and an electrical conductor element, according to an embodiment of the invention.

FIG. 8 is an illustration of a cross-section of another embodiment of a clot removal apparatus 200a comprising a shape memory element 802, a heating element 804, an insulation element 808, a fluid channel or lumen 810, and one or more electrical conductor element 806. This embodiment of the clot removal apparatus 200a and may further comprise radiopaque markers 812 fabricated from materials such as, but not limited to, tantalum, platinum, iridium, gold, and the like. These radiopaque markers 812 can have a thickness ranging from 0.0005 to 0.020 inches. The radiopaque markers 812 can be circumferential bands, or discreet masses of radiodense materials that are readily visible under fluoroscopy and which are embedded in the structures 802 or 808 comprising the wall of the catheter 200. The heating element 804 can comprise high resistance materials such as ceramics and metals such as, but not limited to, nickel chromium wire, tungsten wire, and the like. In an embodiment, the insulation element 808 is electrically insulating. In another embodiment, the insulation element 808 can be thermally insulating to minimize heating effects on surrounding tissue. The Shape memory element 802 is illustrated as a cylinder or tubular structure and encloses the heating element 804 to further dissipate heating effects of the heating element. In an embodiment, the electrical conductor element 806 delivers energy to the distal end of the heating element 804. In another embodiment, the heating element 804 is surrounded by electrical insulation and is doubled up so that both electrical connections are made at the proximal end of the clot removal wire 200. A plurality of electrical conductors 806 can be used to activate multiple coils, for example the proximal coil 700 and the distal coil 400. In an embodiment a separate electrical insulator surrounds the entirety, a portion of, or the exterior of electrical conductor 806.

The shape memory element 802 can be configured as a solid wire or it can be a tubular structure. A tubular structure can be configured to impart more force than a solid wire structure given the same cross-sectional area. Referring to FIG. 11, in yet another embodiment, the shape memory element 802 can be a secondary coil 1104 or 1106. The secondary coil 1104, 1106 can be wound around the core wire, heating element 804. The fluid lumen 810 can be used to even the heating pattern of the heating elements 804, of which two are shown in FIG. 8, or it can be used for purging, aspiration, infusion, or withdrawal of fluids to or from the patient. The fluid lumen 810 can be operably connected to a fluid infusion port (FIG. 10) at the proximal end of the clot removal wire 200. The outer diameter of the clot removal wire 200 can range from 0.004 inches to 0.050 inches and preferably range from 0.006 inches to 0.040 inches in diameter.

Figure 9:
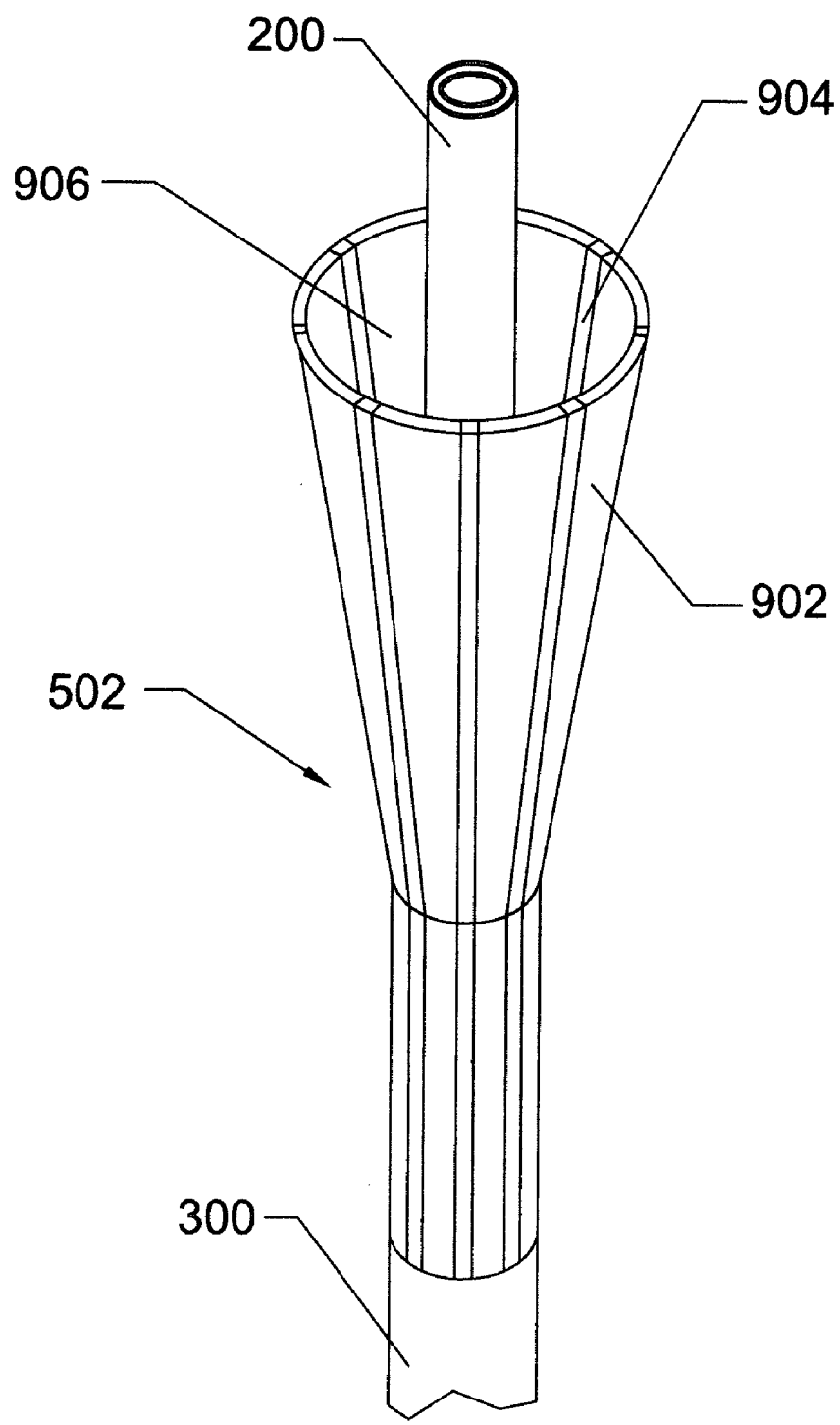
FIG. 9 is an oblique illustration of an expandable distal tip of a coaxial receiving catheter, according to an embodiment of the invention.

FIG. 9 is an oblique illustration of an expandable distal region 502 of a coaxial receiving catheter 300. In an embodiment, the expandable region 502 comprises longitudinal stringers, battens, fingers, plates, wires, or the like 904. The longitudinal stringers 904 are configured to maintain column strength to prevent axial collapse of the expandable distal region 502 when a clot removal coil 400 is withdrawn therein.

The region between the longitudinal stringers 904 comprises elastomeric, furled, longitudinally folded, or non-elastomeric, polymers capable of expanding in circumference. Such expansion can be uniform along the length of the expandable region 502, as shown in FIG. 6 or it can be funnel shaped as shown in FIG. 9. Other configurations for the shape of the expandable region 502 can also be useful. The expandable region 502 can also be configured as a cylindrical shutter structure or iris that expands when the proximal end is rotated relative to the distal end. The stringers 904 can be fabricated from polymers such as, but not limited to, polyester, polyimide, polyamide, PEEK, Hytrel, or the like. The stringers 904 can also comprise metals such as, but not limited to, nitinol, stainless steel, tantalum, platinum, titanium, or the like. The thickness of the stringers 904 can range from about 0.010 inches to about 0 inches smaller than the wall thickness 902 of the catheter 502.

Figure 10:
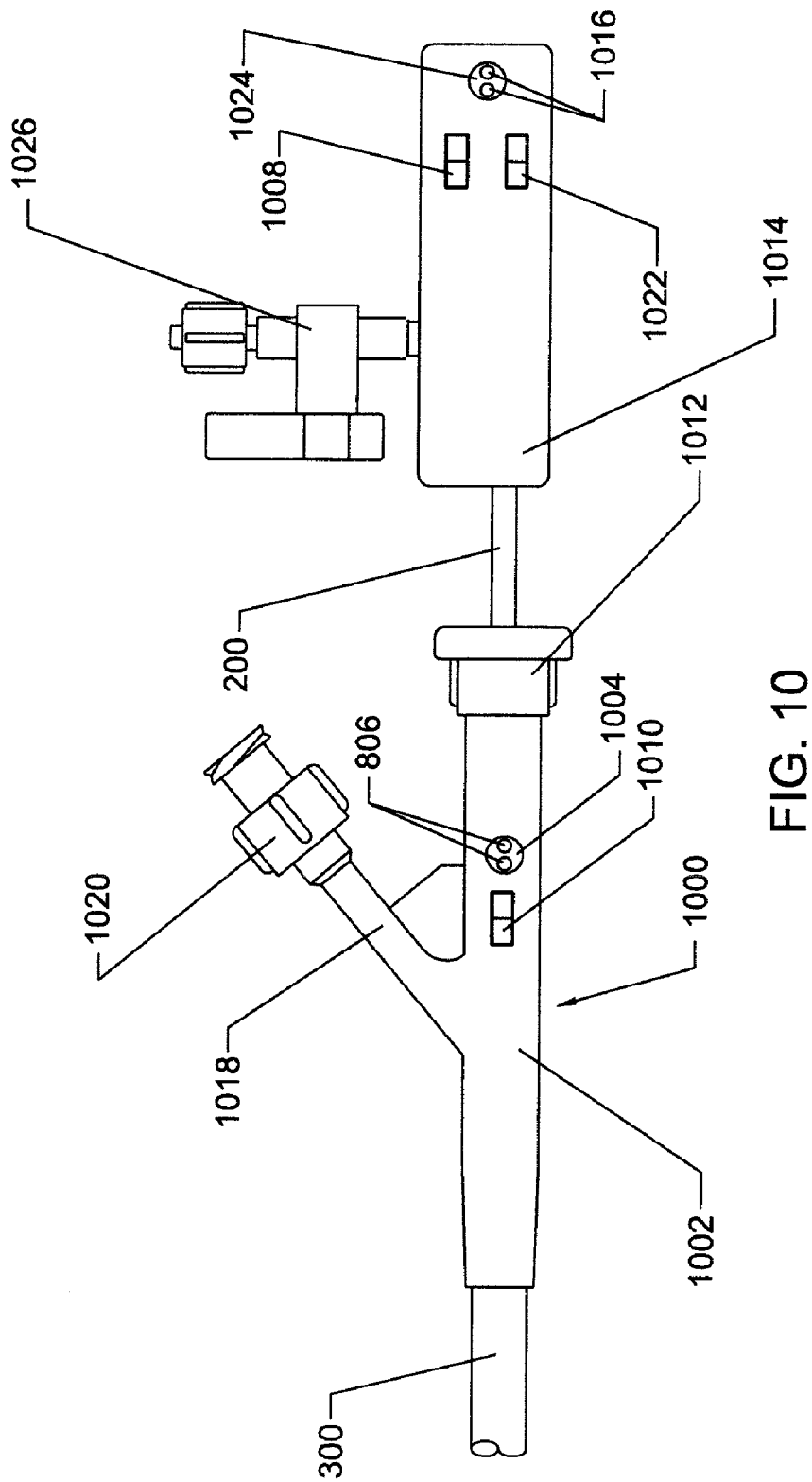
FIG. 10 illustrates the proximal end of a clot removal apparatus 1000, according to an embodiment of the invention.
Figure 11:
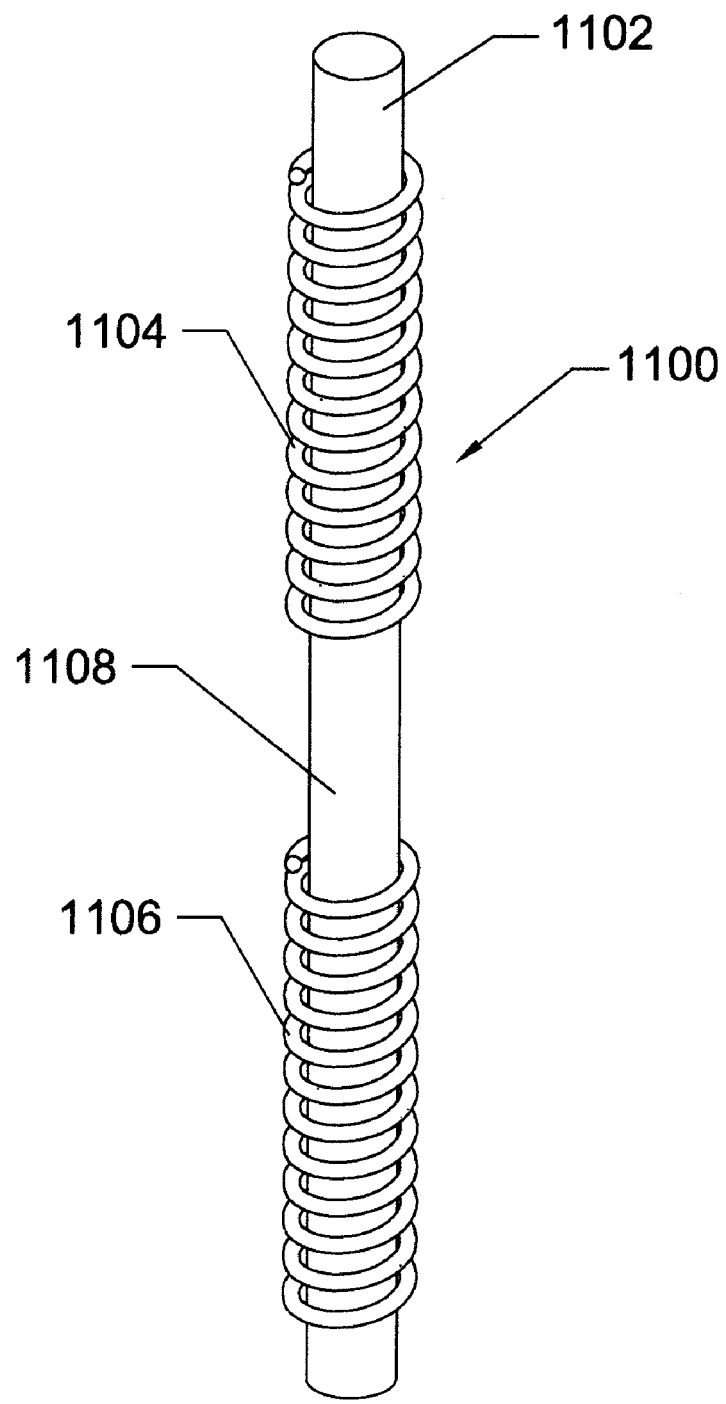
FIG. 11 illustrates a composite clot removal wire construction, according to an embodiment of the invention.

FIG. 10 illustrates the proximal end of a clot removal apparatus 1000 comprising a clot removal wire 200, a receiving catheter 300, a catheter hub 1002, a wire hub 1014, a wire electrical connection 1024, a catheter electrical bus 806, a wire electrical bus 1016, a catheter expansion switch 1008, a clot retrieval activation switch 1010, a secondary coil expansion switch 1022, a catheter electrical connection 1004, and a hemostasis valve 1012. The catheter hub 1002 further comprises a sideport 1018 with a valve 1020. The wire hub 1014 can further comprise an inlet port with valve 1026. The hemostasis valve 1012 comprises a variable diameter central lumen (not shown) capable of accepting and sealing against guidewires, the clot retrieval wire 200, or sealing without anything inserted therethrough.

The catheter hub 1002 is affixed to the proximal end of the catheter tubing 300. The wire hub 1014 is affixed to the proximal end of the clot removal wire 200. The Hemostasis valve 1012, affixed or integral to the catheter hub 1002 can be a Tuohy-Borst valve, slit valve, duckbill valve, a ball valve, a gate valve, a membrane with a closeable hole therein, or a combination of these. The wire electrical input connector 1024 can comprise one or a plurality of electrical bus leads 1016, which would be advantageously electrically insulated from each other. The wire hub 1014 can further comprise electrical switches, for example a switch 1008 to enable the distal coil formation and a switch 1022 to enable proximal coil formation. The wire hub 1014 can comprise temperature readouts, for example gauges or digital displays, operably connected to thermocouples or thermistors affixed at or near the distal end of the wire in important temperature measurement regions. Referring to FIG. 7, the distal coil enable switch 1008 and the proximal coil enable switch 1022 are operably connected to the electrical bus 1016, from which the switches draw power, when closed to activate their respective coils 400 and 700 at the distal end of the wire 200. The wire electrical connector 1024, in an embodiment, can be operably connected to an external power source, for example about 1.5 VDC to 24 Volts DC, or alternating power sources with output levels up to 220 VAC. In another embodiment, the wire electrical connector 1024 can be operably connected to batteries housed externally or internally to the wire hub 1014. The catheter hub 1002 can have its electrical connector 1004 similarly connected to an external electrical power supply or to an internal battery power supply.

The catheter hub 1002 can have a sideport 1018 with a valve 1020 affixed thereto. The sideport 1018 and valve 1020 can be used for advancement of secondary catheters, or for the infusion and withdrawal of fluids from a lumen 906 within the catheter 300. The catheter hub 1002 and the wire hub 1014 can be fabricated from polymers including, but not limited to, polyurethane, polyethylene, polycarbonate, PEBAX, PEEK, Hytrel, polysulfone, or the like. The wire hub 1014 can have affixed, thereto, the fluid infusion or withdrawal port 1026 which can further be terminated with a valve. The fluid infusion or withdrawal port 1026 can be directly affixed to the wire hub 1014 or it can further comprise a length of tubing (not shown) having a central lumen in communication with the port 1026 and a lumen within the wire (not shown). The fluid infusion or withdrawal port 1026 can further be operably connected to a dilation balloon suitable for expanding the distal end 502 of the catheter 300.

FIG. 11 illustrates an alternative embodiment of a clot removal wire 1100. The clot removal wire 1100 comprises a core wire 1102, and a first surrounding coil 1104 and a second surrounding coil 1106. The surrounding coil 1104 can extend the entire length of the core wire 1102 or it can be separated from coil 1106 by a gap 1108. The clot removal wire 1100 can comprise one coil 1104, two coils 1104 and 1106 as illustrated, or it can comprise a plurality of coils (n≧2) separated by a plurality of gaps 1108. This segmented construction is advantageous in that it possesses column strength, bendability, shape control, and kink resistance. The core wire 1102 can comprise a shape memory element or materials or the coil 1104 can comprise shape memory materials, coil 1106 can comprise shape memory materials, or all coils can comprise shape memory materials. The transition temperatures of each coil can be substantially the same or they can be different to allow the clot removal wire 1100 to assume various shapes. In an embodiment, when an energy source can be applied to the shape memory wire 1100, the shape memory element temperatures rise above a given transition temperature and move to reconfigure toward pre-set shapes. In an embodiment, when the energy source is removed from the shape memory wire 1100, the coils 1104 and 1106, for example, cool below their martensite finish ($M_f$) temperature and become softer, thus allowing the core wire 1102, which can be elastomeric, to overpower the coils 1104 and 1106 and return the clot removal wire 1100 to its original approximately straight shape.

Another aspect of the invention is the method of use. The target site is initially diagnosed using fluoroscopy, angiography, magnetic resonance imaging, ultrasound, and the like. In a primary example, the target site is a region of occlusion within the cerebrovasculature. In a suitable catheterization laboratory, under sterile conditions, a Seldinger technique is applied to gain guidewire access to a vessel, for example the right or left femoral artery. The guidewire is routed to the site of the target lesion 106 within the target vessel 100, often more than 100 cm distant from the access site. The catheter 300 is advanced over the guidewire and the guidewire is removed. The clot removal wire 200 is advanced through the catheter 300 until it reaches the target site in the vessel 100. The clot removal wire 200 is advanced across the lesion 106. The clot removal wire 200 is reconfigured into a coil 400 at its distal end by applying electrical power at the proximal end or by the application of radio frequency (RF), HIFU, microwave, or other energy at the distal end within the body. The distal coil 400 is withdrawn with the clot removal wire 200 proximally toward the catheter 300. The distal coil 400 excises from the vessel wall and removes some, or all, of the lesion 106. The entire clot 500 excised from the lesion 106 can be pulled out of the patient along with the catheter 300 or it can be first withdrawn within the distal end 502 of the catheter 300. The distal end 502 is preferably radially expandable and such expansion can be actively performed at the proximal end of the sheath or catheter 300 by application of electrical energy, or using the same techniques discussed previously about activating the distal end using HIFU, microwaves, RF energy, or the like. Other regions of occlusion suitable for treatment using the means described herein include blockages of the coronary arteries, the pulmonary vasculature, or the like.

The distal coil 400, shown in FIG. 4, can be expanded by heating the shape memory material comprising the coil above its austenite finish temperature. The distal coil 400 can be contracted or straightened out by cooling the shape memory material. In an embodiment, the distal coil 400 is allowed to cool and re-shape itself into a straight configuration once the excised clot 500 is safely retrieved within the distal region 502 of the catheter 300. In another embodiment, the distal coil 400, the proximal coil 700, or both, can comprise superelastic materials and be enshrouded within a sleeve to maintain a straight shape. When the sleeve is withdrawn proximally relative to the coil wire, the superelastic coils can form. The coils 400 and 700 can be used to clean obstructions within the vessel in the same way as coils 400 and 700, which are shape-memory in nature.

Figure 12A:
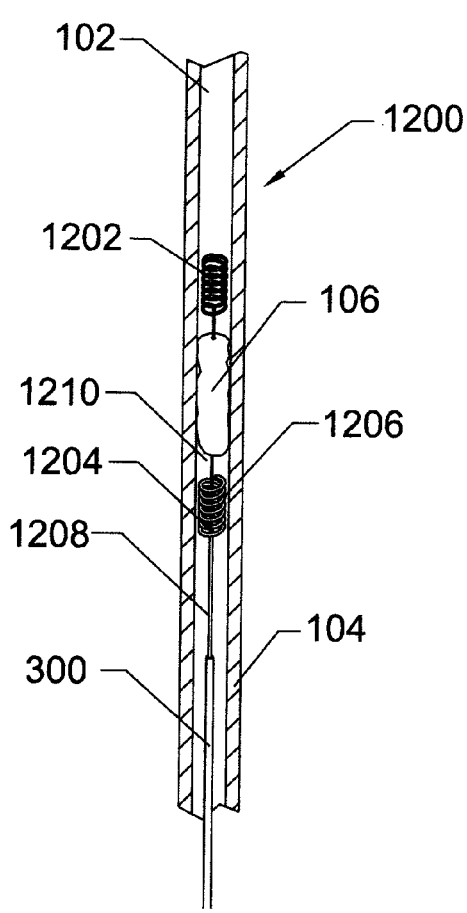
FIG. 12a illustrates a double coil clot removal system wherein the distal coil can be withdrawn proximally toward the proximal coil, according to an embodiment of the invention.

FIG. 12*a* illustrates a dual coil clot retrieval system 1200 comprising a catheter 300, a proximal coil 1206, a distal coil 1202, a port 1204 in a hollow delivery wire 1208 for the proximal coil 1206, and a distal coil delivery wire 1210. The system 1200 is resident in the blood vessel 104 comprising the lumen 102.

The distal coil is illustrated having passed distally to the occlusion 106 but the spacing between the two coils 1202 and 1206 exceeds the length of the obstruction 106. The distal coil delivery wire 1210 is radially constrained by and longitudinally movable within the lumen of the hollow proximal coil delivery wire 1208 by control exerted on a hub affixed to the proximal end of the hollow delivery wire 1208.

Figure 12B:
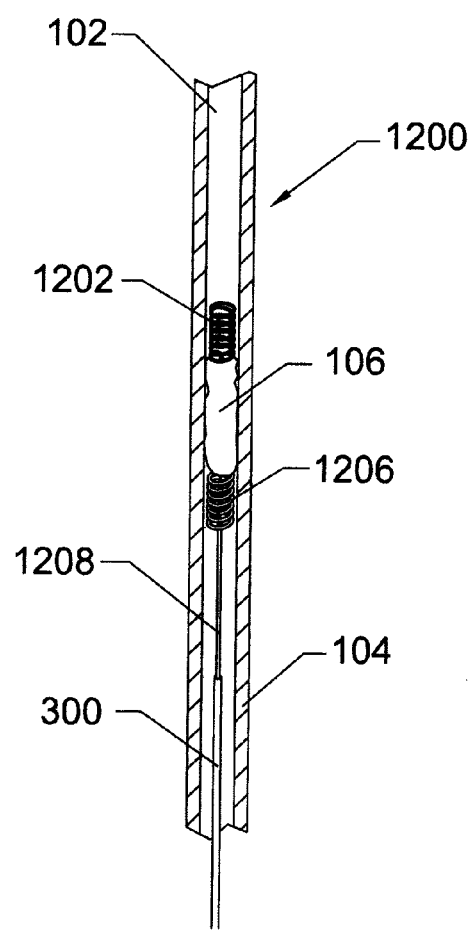
FIG. 12b illustrates the double coil clot removal system of FIG. 12a wherein the two coils have been brought closer together to clamp the clot prior to removal, according to an embodiment of the invention.

FIG. 12*b* illustrates the dual coil clot retrieval system 1200 wherein the distal coil 1202 has been withdrawn proximally toward the proximal coil 1206 to trap the thrombus or occlusion 106 at both ends. In this configuration, the entire system 1200 with trapped clot 106 can be withdrawn proximally into a receiving catheter located within the vessel lumen 102 surrounded by the vessel wall 104.

The method of using the obstruction removal system can comprise the steps of inserting an axially elongate obstruction removal wire into a body vessel or lumen, wherein the obstruction removal wire comprises a proximal end, a distal end, and a longitudinal axis, routing the obstruction removal wire to the region of a target obstruction within a body vessel or lumen in a generally straight configuration, advancing the obstruction removal wire through the target obstruction so that a pre-defined expansible region of the obstruction removal wire, proximate the distal end of the obstruction removal wire, extends beyond the obstruction, applying energy to the obstruction removal wire, transmitting the energy to the pre-defined expansible region, deforming the pre-defined expansible region into a substantially non-straight configuration, and withdrawing the expansible region proximally to remove at least a portion of the target obstruction. The method can further comprise the step of removing the obstruction removal system from the patient. The method can further comprise the step first routing an axially elongate guide catheter to the site of the lesion, removing any guidewires, and then inserting the obstruction removal system, clot removal system, clot removal system, or the like, through the guide catheter. The method can further comprise the step of expanding the distal end of the guide catheter. The method can further comprise the step of removing the guide catheter from the body vessel or lumen of the patient.

The present invention may be embodied in other specific forms without departing from its spirit or essential characteristics. For example, the clot removal system can expand within the obstructive clot, or it can expand distal to the obstructive clot and be withdrawn against the clot. A catheter can be used to envelop and retrieve the removed obstruction; it can be used to guide the clot removal apparatus into place; or both. The embodiments described herein further are suitable for fabricating very small diameter catheters, microcatheters, or sheaths suitable for cardiovascular or neurovascular access. Various valve configurations and radiopaque marker configurations are appropriate for use in this device. The distal coil and the proximal coil can be used, alone or in combination, to ensnare and remove an implant such as a stent, embolic coil, or the like. The described embodiments are to be considered in all respects only as illustrative and not restrictive. It is to be further appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims. Thus, the scope of the invention is therefore indicated by the appended claims rather than the foregoing description. All changes that come within the meaning and range of equivalency of the claims are to be embraced within their scope.

What is claimed is:

1. A system for removing thrombus or other obstructive material from body lumen in a human or non-human animal subject, said system comprising:
   a flexible catheter having a lumen and a distal opening in communication with said lumen;
   an elongate member having a distal end, said elongate member being advanceable through the lumen of the catheter and out of the distal opening;
   an obstructive material engaging structure located at or near the distal end of the elongate member, said obstructive material engaging structure comprising a shape memory wire, said shape memory wire comprising a proximal coil segment and a distal coil segment, each of said proximal and distal coil segments being transitionable, in response to energy delivered thereto, from a collapsed, straight configuration to an expanded, coiled configuration; and
   and a source of energy connected to the proximal and distal coil segments and a control operable to i) selectively cause one of the proximal and distal coil segments to expand while the other does not or ii) cause the proximal and distal coil segments to expand at different expansion rates.

2. A system according to claim 1 wherein:
   the source of energy comprises at least one heating element positioned so as to selectively heat said segment of the elongate member, thereby causing only said segment of the elongate member to transition from the collapsed configuration to the expanded configuration.

3. A system according to claim 1 wherein the obstructive material engaging structure forms a generally complex coil shape when in its expanded configuration.

4. A system according to claim 1 wherein at least the distal opening of the catheter is capable of diametric expansion.

5. A system according to claim 4 wherein a distal region of the catheter including the distal opening is capable of selective diametric expansion.

6. A system according to claim 4 wherein said distal region of the catheter undergoes diametric expansion in response to delivery of energy to said distal region and wherein the system further comprises: a source of energy connected to the catheter for delivering energy to energy to said distal region to cause diametric expansion of said distal region.

* * * * *